(12) United States Patent
Guettler et al.

(10) Patent No.: US 8,431,372 B2
(45) Date of Patent: Apr. 30, 2013

(54) FERMENTATION METHOD USING A MAGNESIUM COMPOUND CONTAINING OXYGEN

(75) Inventors: Michael V. Guettler, Holt, MI (US);
Robert J. Hanchar, Charlotte, MI (US);
Denise S. Rumler, Leslie, MI (US);
Susanne Kleff, Okemos, MI (US)

(73) Assignee: MBI International, Lansing, MI (US)

( * ) Notice: Subject to any disclaimer, the term of this patent is extended or adjusted under 35 U.S.C. 154(b) by 725 days.

(21) Appl. No.: 12/488,417

(22) Filed: Jun. 19, 2009

(65) Prior Publication Data
US 2010/0323416 A1 Dec. 23, 2010

(51) Int. Cl.
*C12P 7/40* (2006.01)
*C12N 1/14* (2006.01)
*C12P 1/00* (2006.01)
*C12P 7/00* (2006.01)
*C12P 7/02* (2006.01)
*C12N 1/00* (2006.01)

(52) U.S. Cl.
USPC ............. 435/136; 435/41; 435/132; 435/155; 435/254.1; 435/256.1; 435/256.6

(58) Field of Classification Search .................. None
See application file for complete search history.

(56) References Cited

U.S. PATENT DOCUMENTS

| | | | |
|---|---|---|---|
| 3,063,910 A | 11/1962 | Abe et al. | |
| 4,664,920 A | 5/1987 | Saleeb et al. | |
| 4,877,731 A | 10/1989 | Ling et al. | |
| 5,504,004 A | 4/1996 | Guettler et al. | |
| 5,573,931 A | 11/1996 | Guettler et al. | |
| 5,723,322 A | 3/1998 | Guettler et al. | |
| 6,455,284 B1 | 9/2002 | Gokarn et al. | |
| 7,105,329 B2 | 9/2006 | Zeikus et al. | |
| 7,192,761 B2 | 3/2007 | Zeikus et al. | |
| 2008/0305533 A1* | 12/2008 | Yi et al. ........................ | 435/145 |
| 2009/0053785 A1 | 2/2009 | Kelley et al. | |

FOREIGN PATENT DOCUMENTS

| | | |
|---|---|---|
| EP | 0 289 219 | 11/1988 |
| WO | WO 2009/081012 A2 | 7/2009 |

OTHER PUBLICATIONS

Dollimore, D; Gupta, J.P; Nowell, D.V. "The Thermal Decomposition of Metal Formates. II. Solid State Thermal Decomposition Studies on Magnesium Formate Dehydrate" Thermochimica Acta, May 1979, 30(1-2), pp. 339-350.*
Cao, Ningjun et al.,"Simultaneous Production and Recovery of Fumaric Acid from Immobilized *Rhizopus oryzae* with a Rotary Biofilm Contactor and an Adsorption Column", Applied and Environmental Microbiology (1996) 62 (8), pp. 2926-2931.
Rhodes, R. A. et al.,"Production of Fumaric Acid in 20-Liter Fermentors", Appl. Envir. Microbiol. (1962) 10:9-15.
Roa Engel, C. A. et al., "Fumaric acid production by fermentation", Appl Microbiol Biotechnol (2008) 78:379-389.
International Search Report from corresponding PCT Application No. PCT/US2010/038572 dated Dec. 6, 2010, 6 pages.
Benthin, et al., "Production of optically pure D-lactate by *Lactobacillus bulgaricus* and purification by crystallisation and liquid/liquid extraction", Applied Microbiology and Biotechnology, vol. 42, No. 6, 1995, pp. 826-829.
Engel, et al., "Development of a low ph fermentation strategy for fumaric acid production by *Rhizopus oryzae*", Enzyme and Microbial Technology, vol. 48, No. 1, Jan. 5, 2011, pp. 39-47.
Engel, et al., "Fumaric acid production by fermentation", Applied Microbiology and Biotechnology, vol. 78, No. 3, Jan. 24, 2008, pp. 379-389.
Rhoades, et al., "Production of fumaric Acid by *Rhizopus arrhizus*", Applied Microbiology, vol. 7, 1959, pp. 74-80.
Rhoades, et al., "Production of fumaric acid in 20-Liter Fermentors", Applied Microbiology, vol. 10, Jan. 1962, pp. 9-15.

* cited by examiner

*Primary Examiner* — Chris R Tate
*Assistant Examiner* — Aaron J Kosar
(74) *Attorney, Agent, or Firm* — Dickinson Wright PLLC

(57) ABSTRACT

This invention is directed to methods of obtaining a high quantity of desired acid salt in a form that is relatively easy to recover. Particularly desired as a recovery product is an organic acid. A salt form of the desired organic acid is formed that is relatively high in concentration and that is relatively soluble in an aqueous medium. The method includes a step of fermenting a fermentable carbon source in the fermentation medium in the presence of a magnesium compound containing oxygen.

16 Claims, No Drawings

FERMENTATION METHOD USING A MAGNESIUM COMPOUND CONTAINING OXYGEN

FIELD OF THE INVENTION

This invention concerns a method for producing organic acids. More specifically, this invention is directed to a method of producing salts of organic acids in which the salts are relatively soluble in an aqueous medium.

BACKGROUND OF THE INVENTION

Fermentation processes generally produce end products that typically need to be separated and recovered for further use. In fermentation processes that incorporate the use of a microorganism that can ferment a carbon source to form an acid type product, it is often difficult to get the desired end product at a sufficiently desirable concentration and in a form that is reasonably efficient to separate and recover.

Rhodes, R A, Lagoda, A A, Misenheimer, T J, Smith, M L, Anderson, R F, and Jackson, R W, Production of Fumaric Acid in 20-Liter Fermentors, *Appl Microbiol* 10:9-15 (1962), describe some of the problems associated with producing a particular organic acid, fumaric acid. The Rhodes article discloses a variety of fermentation methods in which glucose was fermented with *Rhizopus arrhizus* to produce fumaric acid. The fermentations were carried out so as to form calcium, sodium and potassium salts of the acid. Calcium fumarate was produced at a significantly higher concentration compared to the sodium and potassium salt forms. The calcium salt form was found to be insoluble and to lead to a thixotropic broth. The sodium and potassium salt forms were found to be soluble, but the fermentation was inhibited when the concentration of fumarate salts reached 3.5 to 4.0%.

U.S. Pat. No. 4,877,731, discloses a fermentation process for producing carboxylic acids. The process includes growing fungi of the genus *Rhizopus* in a culture medium containing a carbon source, a nitrogen source and inorganic salts, under conditions of controlled oxygen availability wherein the dissolved oxygen concentration for the cell growth phase is between 80% and 100% and where the dissolved oxygen concentration for the acid production phase is between 30% and 80%. To realize the benefit of the invention, it is necessary to add calcium carbonate to the culture medium.

It would be desirable to find alternative or additional methods of producing organic acids at relatively high acid concentrations. It would be further desirable to produce organic acids using a process in which it is relatively easy to separate and recover the desired acid component.

SUMMARY OF THE INVENTION

This invention provides a method of producing an organic acid at a relatively high concentration. The acids that are produced can also be relatively easily separated and recovered.

According to one aspect of this invention, there is provided a method for producing an acid salt. The method comprises obtaining a fermentation medium that contains a fermentable carbon source. The fermentable carbon source is fermented in the fermentation medium to produce the acid salt, with fermenting being carried out in the presence of a magnesium compound that contains oxygen to produce the acid salt. The salt preferably contains a magnesium acid salt, i.e., the magnesium salt of the acid produced during fermentation.

In one embodiment, the fermenting is carried out in the presence of a microorganism that produces at least one acid selected from the group consisting of lactic acid, oxalic acid, oxaloacetic acid, malic acid, fumaric acid, itaconic acid and citric acid. In another, the fermenting is carried out in the presence of a microorganism that actively expresses at least one enzyme selected from the group consisting of lactate dehydrogenase, pyruvate carboxylase, phosphoenolpyruvate carboxykinase, phosphoenolpyruvate carboxylase, and malic enzyme.

In another embodiment of the invention, the fermentation medium is maintained during fermenting at a mole fraction of at least 0.1 of $HCO_3^-$, based on a total concentration of $HCO_3^-$, $CO_2$ and $CO_3^{-2}$ in the fermentation medium. Preferably, $CO_2$ is added to the fermentation medium during fermenting.

In yet another embodiment of the invention, the fermenting is carried out at a pH of at least 5. Preferably the fermenting is carried out at a pH of from 5 to 8, more preferably at a pH of from 6.0 to 7.0.

In another embodiment, the magnesium compound containing oxygen is magnesium oxide, magnesium hydroxide, magnesium bicarbonate, or magnesium carbonate.

According to another aspect of the invention, there is provided a method for producing an acid. The method comprises obtaining a fermentation medium that contains a fermentable carbon source. The fermentable carbon source is fermented in the fermentation medium in the presence of a magnesium compound containing oxygen to produce a liquor that contains a magnesium acid salt form of the acid. A liquid portion is separated from the liquor in which the liquid portion contains at least a majority of the magnesium acid salt; and the pH of the liquid portion is reduced to separate at least a portion of the magnesium from the magnesium acid salt and produce the acid.

In a particular embodiment, the pH is reduced to below at least a first pKa of the acid portion of the magnesium acid salt. Preferably, the liquid portion is maintained at a temperature of not greater than 40° C. during pH reduction or following pH reduction to further concentrate the acid formed from the magnesium acid salt.

In another embodiment, the acid is selected from the group consisting of lactic acid, oxalic acid, oxaloacetic acid, malic acid, fumaric acid, itaconic acid and citric acid.

In yet another embodiment, fermenting is further carried out in the presence of a microorganism that actively expresses at least one enzyme selected from the group consisting of lactate dehydrogenase, pyruvate carboxylase, phosphoenolpyruvate carboxykinase, phosphoenolpyruvate carboxylase, and malic enzyme to form the acid salt.

According to yet another embodiment of the invention, there is provided a method for producing an acid salt such that the acid salt is produced from a fermentable carbon source in a fermentation medium in the presence of a magnesium compound that contains oxygen. Preferably, $CO_2$ is added to the fermentation medium during fermenting to maintain the fermentation medium at a mole fraction of at least 0.1 of $HCO_3^-$, based on a total concentration of $HCO_3^-$, $CO_2$ and $CO_3^{-2}$ in the fermentation medium.

DETAILED DESCRIPTION OF THE INVENTION

I. Production of Product in Soluble Salt Form

This invention provides a way of obtaining a high quantity of desired acid salt in a form that is reasonably easy to recover. Particularly desired as the final product is an organic acid. The organic acid that is preferred for production according to this invention is a $C_2$-$C_6$ acid. In one embodiment, the organic acid is a di-acid or a tri-acid, preferably a di-acid. The organic acid can be saturated or unsaturated. In a particular embodiment, the organic acid is a $C_4$ di-acid. The invention is particularly suited for the production of an acid selected from the group consisting of lactic acid, oxalic acid, oxaloacetic acid, malic acid, fumaric acid, itaconic acid and citric acid.

The product produced from the microorganism used in this invention is converted to a salt form using a magnesium compound containing oxygen. The use of the magnesium compound results in the formation of the desired product at a relatively high conversion and concentration, and in a form that is relatively easy to separate and recover. In particular, the desired product is an organic acid that is relatively soluble in an aqueous medium in its salt form.

The process of this invention provides a product that is particularly high in concentration. For example, the process can provide an acid salt that has a total acid concentration of at least 5 wt %, preferably at least 6 wt %, and more preferably at least 7 wt %, based on total weight of the liquor.

II. Fermentation Medium

The product produced according to the invention is produced by fermenting a fermentable carbon source in an appropriate fermentation medium. The fermentable carbon source used in the practice of this invention can be any carbohydrate that is fermented by a microorganism that is used to form the desired acid product of this invention. The term ferment, fermenting or fermentable is considered to generally refer to an enzymatically controlled transformation of an organic compound, e.g. fermentable carbon source. Such a fermentable carbon source or carbohydrate source includes any one or more of glucose, sucrose, fructose, lactose, soluble starches, pentoses, glycerol, crude biomass hydrolysates, and corn syrups.

The concentration of carbohydrate in the fermentation medium should be sufficiently high to form sufficient quantity of the desired acid product, but not so high as to impede the fermentation process itself. In one embodiment, the concentration of fermentable carbon source in the fermentation medium is from about 20 g/l to about 250 g/l, preferably from about 100 g/l to about 160 g/l.

II. Microorganisms

The particular fermentation process is one that incorporates the use of a microorganism that produces the desired product. In one embodiment, the fermentation process incorporates the use of a microorganism that actively expresses at least one enzyme selected from the group consisting of lactate dehydrogenase, pyruvate carboxylase, phosphoenolpyruvate carboxykinase, phosphoenolpyruvate carboxylase, and malic enzyme. One or more of these enzymes can be used to convert the fermentable carbon source directly or indirectly to the desired end product. In one embodiment, one or more of the enzymes is used to convert the fermentable carbon directly to the desired end product or desired acid composition.

Any organism that naturally expresses one or more of the enzymes used in converting feed into one or more of the acid compositions produced according to the process of this invention can be used. Such organisms include fungi such as *Rhizopus* species and *Aspergillus* species. Non-limiting examples of such species include *R. arrhizus*, *R. oryzae*, and *R. nigricans*. Specific examples include *Rhizopus oryzae (arrhizus)* NRRL 1526, *R. oryzae (arrhizus)* NRRL 2582, *R. oryzae (nigricans)* ATCC 13310, *R. oryzae* NRRL 395, *Aspergillus niger* ATCC 64108, *A. flavus* ATCC 13697, *A. aculeatus* NRRL 358, *A. terreus* NRRL 1960, *A. itaconicus* NRRL 161, *A. sojae* ATCC 46250. Further descriptions of the effects of particular organisms are provided in: Bercovitz et al. (1990), *Localization of Pyruvate Carboxylase in Organic Acid-Producing Aspergillus Strains*, Appl. Environ. Microbiol. 56, 1594-1597; Kenealy W, Zaady E, Dupreez J C, Stieglitz B, Goldberg I *Biochemical Aspects of Fumaric Acid Accumulation by Rhizopus arrhizus.*, Appl. Environ Microbiol. 1986 52, 128-133; Osmani S A, Scrutton M C (1985), *The subcellular localization and regulatory properties of pyruvate carboxylase from Rhizopus arrhizus*. Eur J Biochem 147: 119-128; and Ruijter et al. (2002), *Production of organic acids by fungi*, Mycota 10, 213-230; such descriptions being fully incorporated herein by reference.

Organisms or cells that have been metabolically engineered to actively produce at least one enzyme selected from the group consisting of lactate dehydrogenase, pyruvate carboxylase, phosphoenolpyruvate carboxykinase, phosphoenolpyruvate carboxylase, and malic enzyme can also be used. The metabolically engineered cells can be eukaryotic or prokaryotic. Further descriptions of organisms that have been genetically engineered can be found in Zelle et al. (2008), *Malic Acid Production by Saccharomyces cerevisiae: Engineering of Pyruvate Carboxylation, Oxaloacetate Reduction, and Malate Export*, Appl. Environ. Microbiol. 74, 2766-2777; and Saitoh et al. (2005), *Genetically engineered wine yeast produces high concentrations of L-Lactic acid*, Appl. Environ. Microbiol. 71, 2789-2792; such descriptions being fully incorporated herein by reference.

III. Mg Compound

The fermentation is conducted in a fermentation medium, preferably an aqueous medium, in the presence of a magnesium compound containing oxygen. Preferably, the magnesium compound containing oxygen is at least one compound selected from the group consisting of magnesium oxide, magnesium hydroxide, magnesium bicarbonate and magnesium carbonate.

The magnesium compound containing oxygen is preferably included in the fermentation medium at a concentration to favorably form a salt of the acid product that is produced in the fermentation process. Preferably, the fermentable carbon source is fermented in the fermentation medium in the presence of the magnesium compound, and during fermentation, the fermentation medium is maintained at a mole fraction of at least 0.1 of $HCO_3^-$, based on a total concentration of $HCO_3^-$, $CO_2$ and $CO_3^{-2}$ in the fermentation medium. More preferably, during fermentation, the fermentation medium is maintained at a mole fraction of at least 0.2, and most preferably at least 0.3, of $HCO_3^-$, based on a total concentration of $HCO_3^-$, $CO_2$ and $CO_3^{-2}$ in the fermentation medium.

IV. pH Control

During fermentation, the fermentation medium is maintained at a pH that provides the desired mole fraction of $HCO_3^-$. Providing the desired mole fraction of $HCO_3^-$ results in a high concentration of the desired product. In one embodiment, fermenting is carried out at a pH of at least 5, and most preferably at least 6. In another embodiment, fermenting is carried out at a pH of not greater than 8, preferably not greater than 7.5, more preferably not greater than 7.2. In yet another embodiment, fermenting is carried out at a pH of from 5 to 8, more preferably from 6.0 to 7.0.

In one embodiment, the magnesium compound containing oxygen is added to the fermentation medium at a rate sufficient to maintain the fermentation medium at the desired pH. In a particular embodiment, magnesium carbonate or magnesium hydroxide, more preferably magnesium hydroxide, is added to the fermentation medium at a rate sufficient to maintain the fermentation medium at the desired pH.

V. $CO_2$ Addition

In one embodiment, carbon dioxide is further added to the fermentation medium. Carbon dioxide can be supplied to the fermentation medium in various ways. For example, carbon dioxide can be added to the medium in a mineral carbonate form, in air, in $CO_2$ enriched air, or directly as pure or substantially pure $CO_2$. In one embodiment a fluid, preferably a gas, containing $CO_2$ is added to the fermentation medium. Preferably, the fluid contains at least 0.05% $CO_2$, more preferably from 0.1% to 60% $CO_2$, based on total volume of the fluid added to the medium. More preferably, the fluid contains from 0.2% to 30% $CO_2$, and most preferably from 0.4% to 15% $CO_2$, based on total volume of the fluid or gas added to the medium. In another embodiment, gas, i.e., a total gas addition that includes $CO_2$, is supplied or added to the medium at a total gas volume rate per volume of fermentation medium of from 0.3 l/l-min to 1.3 l/l-min, preferably from 0.5 l/l-min to 1.0 l/l-min. The gas can be added to the medium from one or more sources. During addition of the $CO_2$, the medium is preferably maintained at a predetermined or preferred pH, and preferably during addition of a magnesium compound that contains oxygen.

In one embodiment, fermentation is carried out in a pressurized reactor that contains carbon dioxide at superatmospheric pressure. The carbon dioxide can be mixed with other gases as long as the gases employed do not interfere with the growth and metabolism of the organism employed. Carbon dioxide can also be supplied to the fermentation medium by the addition of carbonates or bicarbonates which generate this gas under the conditions of the fermentation. The fermentation medium preferably contains dissolved $CO_2$ in equilibrium with a minimum of about 0.1 atmosphere partial pressure of carbon dioxide. In a particular embodiment, the fermentation medium is saturated with carbon dioxide and the atmosphere contains at least about 0.3 atmosphere partial pressure of carbon dioxide.

VI. Recovery of Acid

The organic acid salt or magnesium salt composition that is formed in this invention is preferably separated from at least a portion of the fermentation liquor. As used herein, the term fermentation liquor refers to the entire fermented composition. This would include liquid as well as solid components in the fermentation vessel. In an embodiment, a liquid portion is separated from the liquor in which the liquid portion contains at least a majority of the salt. The salt form is then preferably converted to the acid form of the desired product composition, and the acid form is preferably recovered.

The salt can be separated from the liquor using any suitable means. For example, separation can be accomplished using such means as a clarifier, filter, or centrifuge. Any suitable alternative means can be used.

Following initial separation of the salt from the liquor, the salt is converted to the acid form. In one embodiment, the pH of the liquid portion separated from the liquor is reduced. Preferably, the pH of the liquid portion is reduced so that at least a portion of the salt is converted to its acid form. More preferably the salt is a magnesium salt, and the pH of the liquid portion is reduced so that the magnesium salt is converted to its acid form.

In one embodiment of the invention, an acid having more than one pKa is formed in this invention. Preferably, the salt form of the acid is converted to the acid form by reducing the pH of the liquid portion to below at least a first pKa of the acid form of the salt.

Any appropriate means can be used to reduce the pH of the liquid portion. For example acid addition, cation exchange or electrodialysis can be used. Examples of acids that can be used include hydrochloric acid, phosphoric acid and sulfuric acid.

Typically, during acid treatment or lowering of the pH of the liquid portion to form the acid from the salt, the liquid portion increases in temperature. It is preferred to cool the treated liquid portion. In particular, it is preferred to reduce the temperature of the treated liquid portion to precipitate the desired acid product. In one embodiment, the treated liquid portion is reduced to a temperature or not greater than 40° C., preferably not greater than 30° C., more preferably not greater than 20° C., still more preferably not greater than 10° C., and most preferably not greater than 5° C.

In one embodiment of the invention, the liquid portion is reduced in volume so as to concentrate the acid salt or acid form of the salt. Any suitable means of reducing the volume or concentrate the salt or acid can be used. Such means include distillation and reverse osmosis. In a particular embodiment, the acid salt, preferably magnesium acid salt, is concentrated prior to pH reduction. Preferably, the liquid portion that is separated from the liquor is concentrated such that a majority of the acid or acid salt or both in the liquor precipitates following pH reduction. More preferably, the liquid portion that is separated from the liquor is concentrated such that a majority of the acid or acid salt or both in the liquor precipitates following pH reduction to an average pH that is below at least a first pKa of the acid form of the salt.

After the liquid portion is cooled, a majority of the desired acid product is further separated from the cooled liquid and recovered. Any appropriate means of separation can be used. For example, the acid can be filtered or separated by centrifuge.

VII. Examples

General Methods

Culture Maintenance

*Rhizopus oryzae* (*arrhizus*) NRRL 1526 was obtained from the ARS Culture Collection. Plates were inoculated from frozen spore stock. The strain was grown for spore production on the Stage 1 sporulation medium in 100×15 mm Petri plates for 8 days at 30° C. (Table 1). The spore laden plates were stored at 4° C. prior to use as shake flask inocula. Spore suspensions were made by washing a single sporulation plate with 10 ml of 0.05M potassium phosphate buffer, pH 6.8, and containing 0.1% Tween 80. A platinum loop was used to scrape the agar surface to help free the spores from the plate. *R. oryzae* NRRL 1526 was preserved by adding 0.5 ml of spore suspension to 1.5 ml cryovial containing 0.5 ml of 30% glycerol. The vials were stored frozen at −80° C.

Culture Media

The culture media and conditions used in the Examples that follow are described in Table 1. The fermentation procedures described here were built upon those previously described for the production of fumaric acid by *Rhizopus oryzae* NRRL 1526 and NRRL 2582. See Rhodes R A, Moyer A J, Smith M L, Kelley S E (1959) Production of fumaric acid by *Rhizopus arrhizus*. Appl Microbiol 7:74-80; and Rhodes R A, Lagoda A A, Jackson R W, Misenhei T J, Smith M L, Anderson R F (1962) Production of fumaric acid in 20 liter fermentors, Appl Microbiol 10:9-15.

Fermentors

Stage3 and Stage4 fermentations employed the New Brunswick Bioflo III fermentor system with built in pH and dissolved oxygen (DO) control. The Bioflo III 5 liter vessels were equipped with two six-blade Rushton impellers, and the initial medium volume was 4.5 L. The Bio-Command Fermentation software did supervisory control of the Bioflo III systems and logged the process data (www.nbsc.com). The pH was controlled at setpoints between 6.0 and 7.2 with the automatic proportional-integral (PI) addition of a $Mg(OH)_2/H_2O$ slurry that contained 5 moles of $Mg(OH)_2$ per liter of volume. Alternatively, 10M solutions of NaOH or KOH were used for comparison purposes. The DO was maintained near 80% of saturation by control of the agitation between 400-800 rpm. Aeration was 0.44-0.5 l/l-min. The addition of $CO_2$ to the fermentation aeration stream was done with a Brooks 5860i mass flow controller (www.brooksinstrument.com). The Bio-Command fermentation software was programmed to add $CO_2$ into the aeration stream at specified times during the fermentation.

Preparation of Inoculum

The Stage2 inoculum, or spore-germinated inoculum was prepared in shake flasks with solid $MgCO_3$ to help control the pH. Spores were harvested from plates and suspended in 30 ml of 0.05M potassium phosphate buffer, pH 6.8, and containing 0.1% Tween 80. A 500 ml Kimax indented culture flask (#25630) containing 180 ml of Stage2 germination medium was inoculated with 30 ml of the spore suspension. The Stage2 flasks contained about $5 \times 10^6$ spores per ml by direct counts. The flasks were incubated at 32° C. and 250 rpm in an orbital incubator-shaker. Spores were allowed to germinate for 3 hours; at 3 hours 0.5 g of solid $MgCO_3$ was added to buffer the pH for growth. After approximately 14 hours incubation growth stops, the $MgCO_3$ was fully consumed, and the culture will have reached a pH of 3.0-3.2. The culture contains a heavy, dispersible, un-entangled, mycelial growth that can be easily pipetted.

The Stage3 vegetative inocula were grown in fermentors and were started with 5% of the Stage2 spore-germinated inoculum. The aeration in the Stage3 inoculum fermentor was $CO_2$/Air, 0.044 l/l-min $CO_2$ and 0.44 l/l-min Air. The dissolved oxygen (DO) setpoint was maintained at 80% and the agitation was controlled between 400-800 RPM. The pH was maintained at 6.4 with the automatic addition of $Mg(OH)_2$. The morphology of the fungus changed to granular in the Stage3 fermentor after approximately 12 hours of growth. At 14 hours, the Stage3 vegetative inoculum was transferred to the Stage4 production fermentor as a 5% inoculum.

Production Fermentation

The Stage4 fermentation medium contained less $(NH_4)_2SO_4$ than the Stage3 inoculum medium, and fumaric acid production began as the growth ended due to nitrogen depletion. The dissolved oxygen (DO) setpoint was 80% and the agitation was controlled between 400-800 RPM during the growth and production phase. During the first 11.5 hours of growth aeration was 0.44 l/l-min air, and then $CO_2$ was gradually added to the aeration stream over the course of one hour. At 12.5 hours, the aeration stream consisted of 0.44 l/l-min Air and 0.044 l/l-min $CO_2$. This $CO_2$/Air aeration scheme was maintained through the remainder of the growth phase, and throughout the production phase.

Analysis

Carboxylic acid, glycerol, ethanol, and residual glucose concentrations were determined by ion exchange HPLC. Determinations were done with the Waters Breeze HPLC system and the Rezex ROA organic acid column, 300×7.8 mm. The column temperature was 50° C., and mobile phase was 0.012 N H2SO4 with a flow rate of 0.4 ml/min. Detection of sugars, organic acids, and alcohols was with the Waters 2414 refractive index system.

TABLE 1

Media and Conditions.

| | Inoculum development | | Fermentation | | |
| --- | --- | --- | --- | --- | --- |
| Ingredient | Stage1 Sporulation | Stage2 Germination | Stage3 Vegetative | Stage4 Production | Unit |
| Glucose | 4 | 40 | 160 | 160 | g/l |
| $CaCO_3$ | 3 | — | — | — | g/l |
| $MgCO_3$ | — | 2.5 | — | — | g/l |
| Lactose | 6 | — | — | — | g/l |
| Glycerol | 10 (ml) | — | — | — | ml/l |
| Urea | 0.6 | — | — | — | g/l |
| Corn-steep liquor | 1 (ml) | 0.5 (ml) | 0.5 (ml) | 0.5 (ml) | ml/l |
| $KH_2PO_4$ | 0.4 | 1.6 | 1.6 | 1.6 | g/l |
| $MgSO_4$ | 0.145 | 0.195 | 0.195 | 0.195 | g/l |
| $ZnSO_4 \cdot 7H_2O$ | 0.088 | 0.044 | 0.044 | 0.044 | g/l |
| Tartaric Acid | 0.0075 | 0.0075 | 0.0075 | 0.0075 | g/l |
| $FeCl_3$ | 0.0045 | 0.0045 | 0.0045 | 0.0045 | g/l |
| $CuSO_4$ | 0.005 | — | — | — | g/l |
| Polyglycol P2000 | — | — | 60[e] | 60[e] | ppm, v/v |
| $MnSO_4 \cdot 4H_2O$ | 0.05 | — | — | — | g/l |
| KCl | 0.4 | — | — | — | g/l |
| NaCl | 40 | — | — | — | g/l |
| Agar | 30 | — | — | — | g/l |
| $(NH_4)_2SO_4$ | — | 4 | 4 | 1.8 | g/l |
| $K_2HPO_4$ | — | 0.128[a] | 0.128 | — | g/l |
| $KH_2PO_4$ | — | 0.104[a] | 0.104 | — | g/l |
| Tween 80[a] | — | 0.03[a] | — | — | g/l |
| pH setpoint | — | — | 6.4 | 6.8 | pH |
| $Mg(OH)_2$ 10N slurry | — | — | +[c] | +[c] | — |
| Inoculum size | Lawn | ~$5 \times 10^6$ spores/ml | 4.4% | 5% | — |

TABLE 1-continued

Media and Conditions.

|  | Inoculum development | | Fermentation | | |
|---|---|---|---|---|---|
| Ingredient | Stage1 Sporulation | Stage2 Germination | Stage3 Vegetative | Stage4 Production | Unit |
| D.O. setpoint | — | — | 80 | 80 | % |
| Air flow | — | — | 0.44 | 0.44 | v.v.m. |
| CO$_2$ feed | — | — | 0.044 | 0.044[b] | v.v.m. |
| Temperature | 30 | 32 | 34 | 34 | ° C. |
| Agitation | — | 250[f] | 400-800[d] | 400-800[d] | RPM |

[a]added as spore wash buffer
[b]begin after 12 hours of growth
[c]P.I. automatic slurry addition
[d]P.I.D. D.O. control
[e]additional ppm added as needed
[f]gyrotatory

Example 1

The Stage3 vegetative inoculum for the 222-09 Stage4 production fermentor was grown with a CO$_2$/Air mixture, while the Stage3 inoculum for the 221-09 production fermentor was grown with air only. This example illustrates the effect of using a Stage3 inoculum developed with a CO$_2$/Air mixture. The acid productivity or space time yield (STY) in the Stage4 fermentation was increased from 0.60 to 0.79 g/l-h, or 31%. The Stage4 fermentations started with a CO$_2$/Air inoculum also produced higher acid concentrations, higher weight yields, and higher acid selectivity.

Example 1: Fumaric acid production results

| Stage4 Fermentation # | Stage3 Inoculum | STY (g/l/h) | Concentration (g/l) | Yield (wt %) | Selectivity (%) | glycerol (g/l) |
|---|---|---|---|---|---|---|
| 222-09 | CO$_2$/Air | 0.79 | 76.9 | 58 | 76 | 13.0 |
| 221-09 | Air only | 0.60 | 74.5 | 55 | 72 | 15.6 |

Stage4 conditions: pH6.4; CO2 at 0 h

Example 2

The Stage3 vegetative inoculum for the 220-09 Stage4 production fermentor was grown with a CO$_2$/Air mixture, while the Stage3 inoculum for the 219-09 production fermentor was grown with air only. This example illustrates the beneficial effect of using an inoculum developed with a CO$_2$/Air mixture, the acid STY in the Stage4 fermentation was increased from 0.59 to 0.95 g/l-h, or 61%. The CO$_2$/Air inoculum also produced higher acid concentrations, higher yields, and higher acid selectivity.

Example 2: Fumaric acid production results

| Stage4 Fermentation # | Stage3 Inoculum | STY (g/l/h) | Concentration (g/l) | Yield (wt %) | Selectivity (%) | glycerol (g/l) |
|---|---|---|---|---|---|---|
| 220-09 | CO$_2$/Air | 0.95 | 76.4 | 59 | 74 | 15.1 |
| 219-09 | Air only | 0.59 | 72.0 | 54 | 71 | 16.0 |

Stage4 conditions: pH6.4; CO2 at 12 h

Example 3

This example illustrates the effect of using Mg$^{++}$ instead of Na$^+$ for the production of a soluble acid salt. Example 4 shows that the acid production was improved if a magnesium containing base was used to produce a soluble acid salt. Higher concentrations of acid were produced with Mg(OH)$_2$. Fermentations in which the pH was maintained at 6.4 with Mg(OH)$_2$ produced 130% more acid concentration than fermentations using sodium hydroxide. The use of the magnesium base increased the acid STY (g/l-h) 296%, the acid weight yield and the selectivity were also higher.

Example 3: Fumaric acid production results

| Fermentation | Base | Concentration (g/l) | Yield (wt %) | STY (g/l-h) | Selectivity (%) | glycerol (g/l) |
|---|---|---|---|---|---|---|
| 220-09 | Mg(OH)$_2$ | 76.4 | 59 | 0.95 | 73.7 | 15.1 |
| 217-09 | NaOH | 32.9 | 32 | 0.24 | 59.3 | 16.0 |

Stage4 conditions: pH 6.4, CO2 at 12 h

Example 4

This example illustrates the effect of using Mg$^{++}$ instead of Na$^+$ or K$^+$ for the production of a soluble acid salt. A higher concentrations of acid was produced in the fermentation in which the pH was maintained at 6.8 with Mg(OH)$_2$. The use of the magnesium base also increased the acid STY, weight yield, and the selectivity. This example also showed that maintaining the pH at a slightly higher value of 6.8 with Mg(OH)$_2$ resulted in further improvement in acid productivity (cf. STY Example 3).

Example 4: Fumaric acid production results

| Fermentation | Base | Concentration (g/l) | Yield (wt %) | STY (g/l-h) | Selectivity (%) | glycerol (g/l) |
|---|---|---|---|---|---|---|
| 303-09 | Mg(OH)$_2$ | 75.4 | 58 | 1.15 | 73.0 | 16.4 |
| 423-09 | NaOH | 27.6 | 24 | 0.29 | 45.6 | 32.5 |
| 424-09 | KOH | 31.6 | 32 | 0.51 | 61.9 | 25.0 |

Stage4 conditions: pH 6.8, CO2 at 12 h

Example 5

This example illustrates the effect of supplying a $CO_2$/Air mixture to the Stage4 production fermentation instead of air alone. The production of soluble magnesium acid salt was improved by adding $CO_2$ to the air supplied to the Stage4 fermentation. The acid concentration was increased by 35%, the acid productivity by 72%. The acid yield and selectivity were also improved.

Example 5: Fumaric acid production results

| Stage4 Fermentation # | pH | $CO_2$ start time (h) | STY (g/l/h) | Concentration (g/L) | Yield (wt %) | Selectivity (%) |
|---|---|---|---|---|---|---|
| 218-09 | 6.4 | none/air only | 0.46 | 56.8 | 42 | 56.7 |
| 222-09 | 6.4 | 0 | 0.79 | 76.9 | 58 | 76.1 |

Example 6

This example illustrates the effect of a differential application of $CO_2$ enriched air to the Stage 4 fermentation. The acid productivity was improved further if the application of $CO_2$ enriched air was limited during growth phase and fully applied during the production phase of the fermentation. When $CO_2$ enriched air was applied after 12 hours of growth the STY was increased from 0.46 to 0.95 g/L-h, or 107%. The productivity improvement in the fermentation in which the $CO_2$ was supplied during the entire fermentation was less, 0.46 to 0.79 g/l-h or 72%.

Example 6: Fumaric acid production results

| Stage4 Fermentation # | pH | $CO_2$ start time (h) | STY (g/l/h) | Concentration (g/L) | Yield (wt %) | Selectivity (%) |
|---|---|---|---|---|---|---|
| 218-09 | 6.4 | none/air only | 0.46 | 56.8 | 42 | 56.7 |
| 222-09 | 6.4 | 0 | 0.79 | 76.9 | 58 | 76.1 |
| 220-09 | 6.4 | 12 | 0.95 | 76.4 | 59 | 73.7 |

Example 7

This example illustrates the beneficial effects of pH control on the acid production. Acid productivity was increased when the fermentation was maintained higher with the automatic addition of $Mg(OH)_2$. The acid productivity was 0.47 g/l-h at pH 6.0, 0.83 g/l-h at pH 6.4, and 1.14 g/l-h at pH 6.8. The acid STY was at a high by controlling the pH at or near pH 6.8 with $Mg(OH)_2$. Examples 4 and 5 (above) showed the improvement in acid production from using $Mg(OH)_2$ instead of NaOH or KOH to maintain the pH.

Example 7: Fumaric acid production results

| Stage4 Fermentation # | pH | STY (g/l-h) | Concentration (g/l) | Yield (wt %) | Selectivity (%) |
|---|---|---|---|---|---|
| 421-09 | 7.2 | 0.99 | 58.5 | 41 | 58.5 |
| 422-09 | 7.2 | 0.98 | 57.1 | 44 | 57.1 |
| Average | | 1.09 | 57.8 | 43 | 57.8 |
| 303-09 | 6.8 | 1.15 | 75.4 | 58 | 73.0 |
| 304-09 | 6.8 | 1.12 | 73.3 | 57 | 71.2 |
| Average | | 1.14 | 74.4 | 58 | 72.1 |
| 305-09 | 6.4 | 0.73 | 74.8 | 58 | 71.2 |
| 306-09 | 6.4 | 0.81 | 75.5 | 58 | 73.0 |
| 220-09 | 6.4 | 0.95 | 76.4 | 59 | 73.7 |
| Average | | 0.83 | 75.6 | 58 | 72.6 |
| 301-09 | 6.0 | 0.47 | 75.0 | 56 | 72.7 |
| 302-09 | 6.0 | 0.48 | 76.9 | 57 | 74.8 |
| Average | | 0.47 | 75.9 | 56 | 73.8 |

Stage4 conditions: $CO_2$ at 12 h

Recovery Example 1

Fumaric acid was recovered from fermentation broth from a *Rhizopus arrhizus* NRRL 1526 fermentation of glucose performed as described herein. The broth contained 73.66 g/l fumaric acid as its soluble magnesium salt. Two liters of the broth was vacuum filtered through a 5.5 cm Whatman #5 filter covered with a 1 cm thick layer of celite. Sulfuric acid was added to the clarified broth until a pH of 0.5 was reached. The slurry was cooled to 4° C. and the precipitated free fumaric acid was collected by vacuum filtration. The collected solid was washed with 150 ml of ice cold water and dried. This gave 139.33 grams of fumaric acid which was 94.8% chemical pure.

Recovery Example 2

Fumaric acid was recovered from fermentation broth (pp) from a *Rhizopus arrhizus* NRRL1526 fermentation of glucose performed as describe herein. The broth contained 58.675 g/l fumaric acid as its soluble magnesium salt. 100.6 Kg of the fermentation broth was gravity filtered through a 24-inch kettle filter fitted with a polypropylene synthetic filter felt with a 5 micron rating. The broth was recycled through the filter until a clear broth was obtained. Concentrated sulfuric acid was added to the clarified broth until a pH of 0.5 was reached. The slurry was cooled to 4° C. and the precipitated free fumaric acid was collected by vacuum filtration. The collected solid was washed and dried to give 5.5 Kg of fumaric acid that was 96.5% chemically pure.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:
1. A method for producing fumaric acid salt, comprising:
   obtaining a fermentation medium that contains a fermentable carbon source; and
   contacting the fermentable carbon source in the fermentation medium with (i) a fumaric acid-producing fungus and (ii) an amount of a magnesium compound sufficient to maintain the pH of the contacted medium at a pH of at least 5, wherein the magnesium compound is selected from the group consisting of magnesium oxide, magne- sium hydroxide, magnesium bicarbonate, magnesium carbonate, and combinations thereof;

fermenting the contacted medium for a period of time and at conditions sufficient to produce a magnesium fumarate salt in the medium; and isolating the magnesium fumarate from the fermentation medium.

2. The method of claim 1, wherein the fermentation medium is maintained during fermenting at a mole fraction of at least 0.1 of $HCO_3^-$, based on a total concentration of $HCO_3^-$, $CO_2$ and $CO_3^{-2}$ in the fermentation medium.

3. The method of claim 1, wherein $CO_2$ is added to the fermentation medium during fermenting.

4. The method of claim 1, wherein the amount of the magnesium compound is sufficient to maintain the pH at a pH of from 5 to 8.

5. The method of claim 4, wherein the amount of the magnesium compound is sufficient to maintain the pH at a pH of from 6.0 to 7.0.

6. The method of claim 1, wherein the fumaric acid-producing fungus is selected from the group consisting of *Rhizopus* species and *Aspergillus* species.

7. The method of claim 6, wherein the fumaric acid-producing fungus is a *Rhizopus* species.

8. A method for producing fumaric acid, comprising:

obtaining a fermentation medium that contains a fermentable carbon source;

contacting the fermentable carbon source in the fermentation medium with (i) a fumaric acid-producing fungus and (ii) an amount of a magnesium compound sufficient to maintain the pH of the contacted medium at a pH of at least 5, wherein the magnesium compound is selected from the group consisting of magnesium oxide, magnesium hydroxide, magnesium bicarbonate, magnesium carbonate, and combinations thereof;

fermenting the contacted medium for a period of time and at conditions sufficient to produce in the medium a liquor containing a magnesium fumarate salt, wherein the liquor comprises a liquid portion, and a majority of the magnesium fumarate salt is contained in the liquid portion;

separating an amount of the liquid portion from the liquor;

reducing the pH of the separated amount of the liquid portion to separate at least a portion of the magnesium from the magnesium acid salt, thereby producing the fumaric acid; and isolating the fumaric acid from the pH-reduced liquid portion.

9. The method of claim 8, wherein the pH is reduced to below at least a first pKa of the acid portion of the magnesium acid salt.

10. The method of claim 8, wherein the liquid portion is maintained at a temperature of not greater than 40° C. during pH reduction or following pH reduction to further concentrate the acid formed from the magnesium acid salt.

11. The method of claim 8, wherein the fermentation medium is maintained during fermenting at a mole fraction of at least 0.1 of $HCO_3^-$, based on a total concentration of $HCO_3^-$, $CO_2$ and $CO_3^{-2}$ in the fermentation medium.

12. The method of claim 8, wherein $CO_2$ is added to the fermentation medium during fermenting.

13. The method of claim 8, wherein the amount of the magnesium compound is sufficient to maintain the pH at a pH of from 5 to 8.

14. The method of claim 13, wherein the amount of the magnesium compound is sufficient to maintain the pH at a pH of from 6.0 to 7.0.

15. The method of claim 8, wherein the fumaric acid-producing fungus is selected from the group consisting of *Rhizopus* species and *Aspergillus* species.

16. The method of claim 15, wherein the fumaric acid-producing fungus is a *Rhizopus* species.

* * * * *